025

(12) United States Patent
Baldwin et al.

(10) Patent No.: US 6,953,450 B2
(45) Date of Patent: Oct. 11, 2005

(54) APPARATUS AND METHOD FOR ADMINISTRATION OF IV LIQUID MEDICATION AND IV FLUSH SOLUTIONS

(75) Inventors: Brian Eugene Baldwin, Centennial, CO (US); Joseph V. Ranalletta, Englewood, CO (US)

(73) Assignee: Baxa Corporation, Englewood, CO (US)

( * ) Notice: Subject to any disclaimer, the term of this patent is extended or adjusted under 35 U.S.C. 154(b) by 0 days.

(21) Appl. No.: 10/225,886

(22) Filed: Aug. 22, 2002

(65) Prior Publication Data

US 2004/0039346 A1 Feb. 26, 2004

(51) Int. Cl.[7] .............................. A61M 5/00; F16D 3/03
(52) U.S. Cl. .............. 604/248; 137/625.23; 137/625.46
(58) Field of Search .............................. 604/30, 32, 80, 604/181, 187, 191, 246, 248, 257, 258, 284, 533, 534, 535, 537, 538, 539; 137/625.21, 625.22, 65.23, 625.24, 625.4, 625.41, 625.42, 625.46, 602, 625.23

(56) References Cited

U.S. PATENT DOCUMENTS

| | | | |
|---|---|---|---|
| 3,344,785 A | 10/1967 | Hamilton | |
| 4,210,173 A | 7/1980 | Choksi et al. | 137/512.3 |
| 4,219,021 A | 8/1980 | Fink | 128/214 |
| 4,253,501 A | 3/1981 | Ogle | 141/27 |
| 4,397,335 A | 8/1983 | Doblar et al. | 137/625.19 |
| 4,563,175 A | 1/1986 | LaFond | 604/155 |
| 4,645,496 A | 2/1987 | Oscarson | 604/148 |
| 4,713,060 A | * 12/1987 | Riuli | 604/199 |
| 4,857,056 A | 8/1989 | Talonn | 604/135 |
| 5,002,528 A | 3/1991 | Palestrant | 604/28 |
| 5,104,387 A | * 4/1992 | Pokorney et al. | 604/248 |
| 5,144,972 A | 9/1992 | Dryden | 137/15 |
| 5,176,658 A | 1/1993 | Ranford | 604/247 |
| 5,318,539 A | 6/1994 | O'Neil | 604/118 |

(Continued)

FOREIGN PATENT DOCUMENTS

| | | |
|---|---|---|
| DE | 441237 | 2/1927 |
| WO | WO 9934846 | 7/1999 |

OTHER PUBLICATIONS

Product Literature by GL Medical, The "Twist–N–Ject" Stopcock, 2 Pages.
Product Instructions by Children's Medical Ventures, Inc., Safe–T–Care Anti–free flow Infusion / Flush Set, 1 Page.
Information Page by Children's Medical Ventures, Inc., Safe–T–Care Infusion Set, www.childmed.com, 2 Pages.
Product Literature by Needle & Infusion Technologies, Inc., Infucare Syringe Pump / Flush Extensions Set for IV Medications, 1 Page.
Product Information Card by Baxter, Interlink Needle–Less IV Access System, 1 Page.
Information Page by Baxter, Interlink Needle–Less IV Access System, www.life–assist.com, 37 Pages.

Primary Examiner—Nicholas D. Lucchesi
Assistant Examiner—Mark K. Han
(74) Attorney, Agent, or Firm—Marsh Fischmann & Breyfogle LLP

(57) ABSTRACT

The present invention provides a medical liquid administration apparatus and administration method that are particularly apt for intravenous (IV) applications. More particularly, the administration apparatus and method may be employed in conjunction with the administration of liquid medication and one or more flush solutions from multi-dose sources, wherein fluid interconnections between at least one flush solution source and the administration apparatus may be established a single time at the outset of a given procedure. The administration apparatus may include a valve having a control member selectively positionable to provide any selected one of a plurality of closed flow paths through the valve, and a syringe interconnected to the control member for clockwise/counterclockwise co-rotation therewith (e.g. to establish the selected flow path).

42 Claims, 10 Drawing Sheets

U.S. PATENT DOCUMENTS

| | | | |
|---|---|---|---|
| 5,336,188 A | 8/1994 | Kriesel | 604/132 |
| 5,419,771 A | 5/1995 | Kriesel | 604/132 |
| 5,439,452 A | 8/1995 | McCarty | 604/186 |
| 5,454,792 A | 10/1995 | Tennican et al. | 604/191 |
| 5,740,810 A | 4/1998 | Johnson et al. | 128/673 |
| 6,086,561 A | 7/2000 | Kriesel et al. | 604/133 |
| 6,457,488 B2 * | 10/2002 | Loo | 137/625.47 |

* cited by examiner

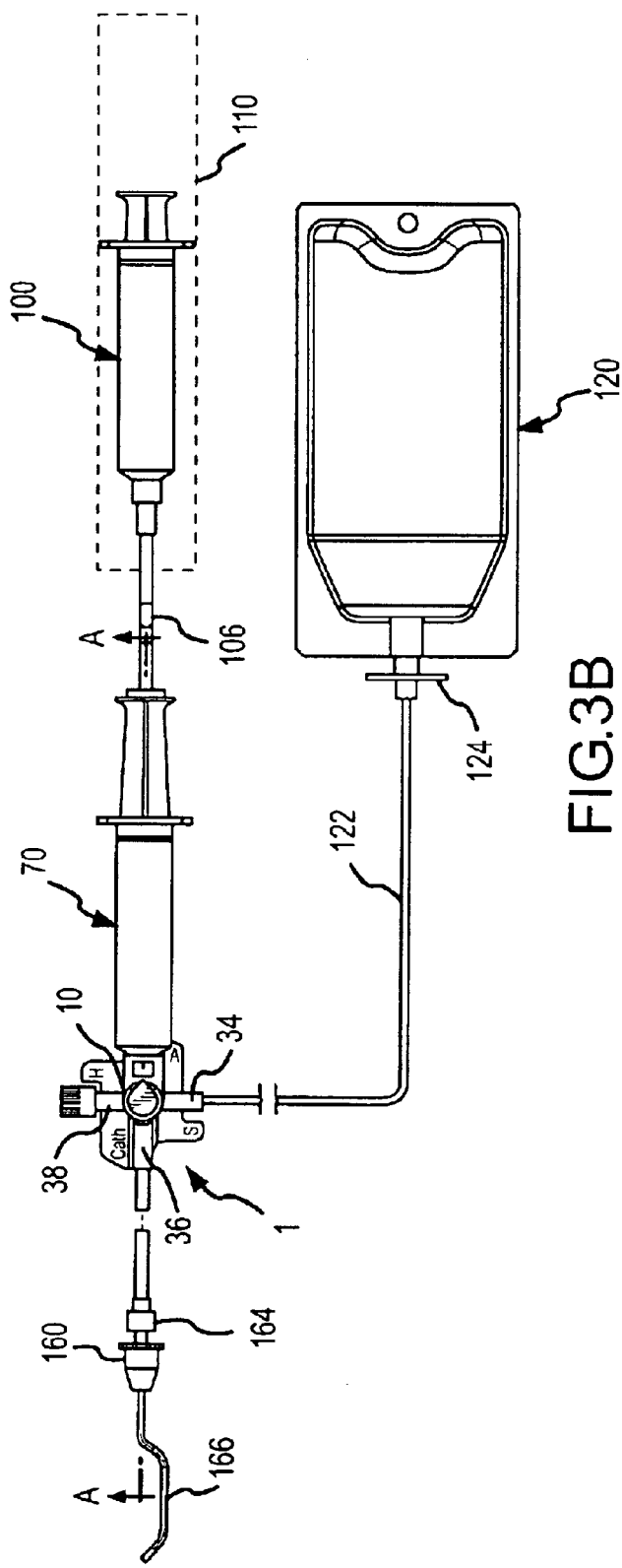
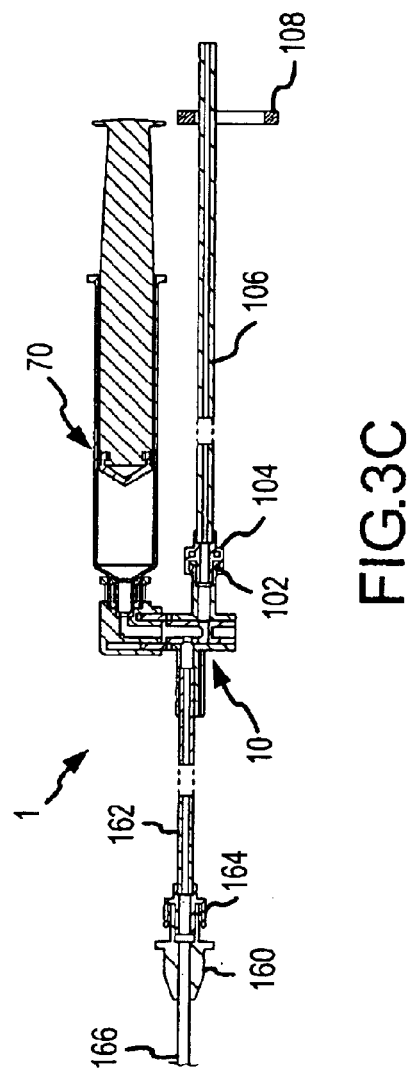
FIG.3B
FIG.3C

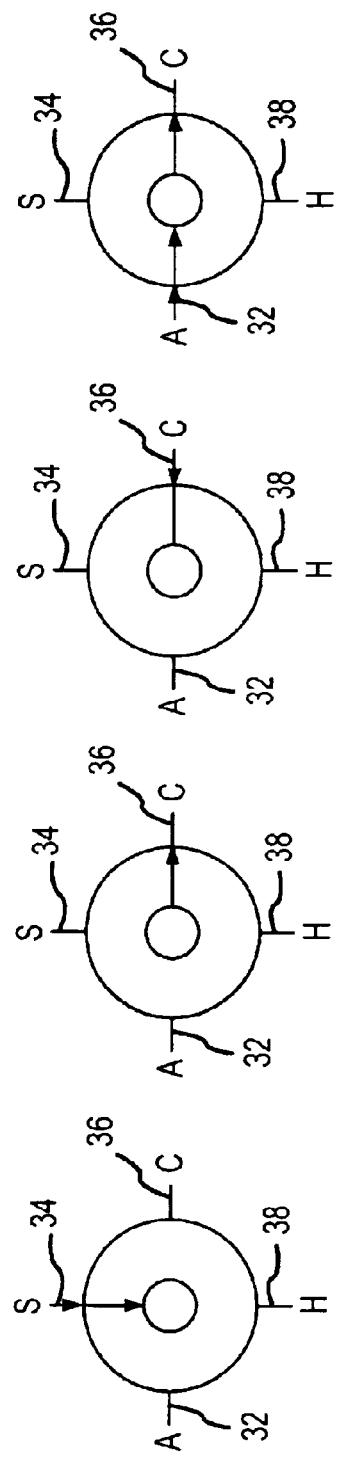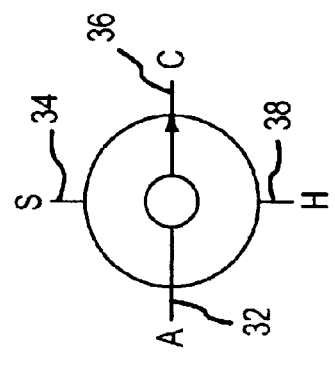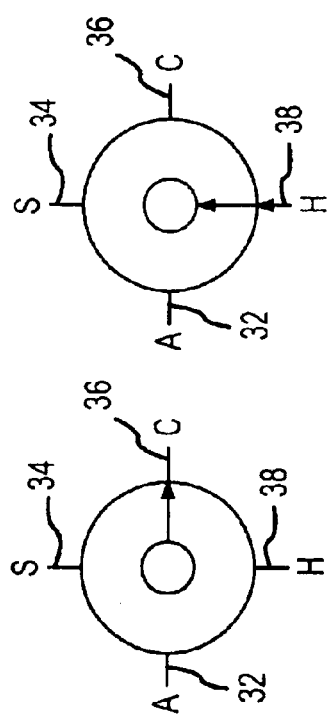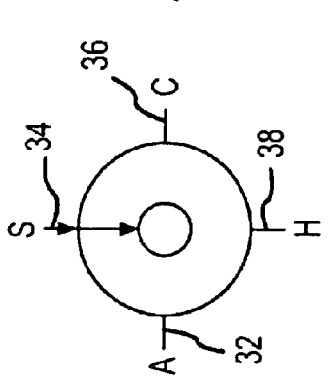

APPARATUS AND METHOD FOR ADMINISTRATION OF IV LIQUID MEDICATION AND IV FLUSH SOLUTIONS

FIELD OF THE INVENTION

The present invention relates to the field of medical liquid administration, and more particularly, to an administration apparatus and method for administering multiple medical liquids during one or repeated periods. The administration apparatus and method are particularly apt for use in successive intravascular (IV) administrations of liquid medication and one or multiple flush solutions over an extended time period, wherein the liquid medication and flush solution(s) may be alternately infused through a closed system requiring only a single vascular catheter fluid interconnection per sequence.

BACKGROUND OF THE INVENTION

Numerous techniques are employed for the administration of "medical liquids" (e.g. liquid medication and flush solutions) to a patient. In particular, where repeated medication infusions are required, medical liquids are often administered via the use of a vascular access catheter that is fluidly interconnected or interconnectable to one or more medical liquid sources via an associated tubing line set. Typically, the catheter is inserted into the vein of a patient and left there for multiple intravenous (IV) infusions during an extended course of medication therapy. By way of example, the time period between IV drug infusions may be between about 4 to 24 hours, wherein the IV liquid medication source is typically replaced after each dose infusion. In the course of extended medication therapy a given tubing line set may be repeatedly employed, and a number of tubing line sets may be successively employed. For example, it is typical to replace a given tubing line set every two or three days.

During extended therapy applications, a desirable practice is to disconnect the vascular catheter from a medical liquid source and tubing line set between infusions. In this regard, most patients receiving IV medication therapy are ambulatory to some degree and benefit from not being continuously connected.

In conjunction with the repeated connection/disconnection of a vascular catheter and liquid medication source and tubing line set, it is usual practice to purge the vascular catheter with a flush solution (e.g. a saline solution) prior to and at the completion of a given liquid medication infusion. Pre-infusion flushing verifies that the vascular catheter is primed and clear of obstructions. Post infusion flushing not only flushes through any remaining liquid medication to achieve the desired therapeutic effect, but also reduces any chance that the vascular catheter may become blocked in-between infusions, e.g. by a blood clot that may otherwise form in the vascular catheter. In relation to infusion procedures, it is also common practice to verify the proper functioning of a vascular catheter via aspiration. This is typically done prior to pre-infusion flushing and after liquid medication infusion. The procedure entails using the flush solution syringe or liquid medication syringe to drain a small amount of a patient's blood through the vascular catheter, thereby permitting visual verification of proper vascular catheter functionability, then advancing the blood back through the vascular catheter using the syringe. By way of example, such procedure assures that the vascular catheter is not blocked by a blood clot and is otherwise properly inserted into a patient's vascular system.

A number of approaches are currently utilized for the noted flushing procedures. Such techniques generally entail the usage of flush solutions packaged in large volume, multi-dose reservoirs (e.g. about 250 ml. or more) or pre-filled unit dose syringes (e.g. having volumes of 2, 3, 5 or 10 ml.).

Where a unit dose syringe is utilized, medical personnel must generally remove the syringe from packaging, remove a cap from the syringe, remove any air in the syringe, swab a vascular catheter access port with an antibacterial material, interconnect the syringe to a vascular catheter access port, optionally aspirate the vascular catheter, advance the syringe plunger to infuse the flush solution (e.g. at a rate of about 5 to 10 ml. over about 15 to 30 seconds), remove the syringe from the vascular catheter access port and discard the used syringe with its wrapper. As may be appreciated, such steps may need to be repeated numerous times over the course of extended medication therapy, e.g. after each infusion and vascular catheter access port reconnection, thereby entailing significant medical personnel time and resulting in substantial medical waste. Further, while unit dose syringes provide good sensitivity for aspiration purposes they are not particularly pressure sensitive for flushing purposes.

Where multi-dose flush solution reservoirs are employed, medical personnel typically utilize an empty unit dose syringe to draw the flush solution from the reservoir, then follow the same basic procedure noted above in an administering the flush solution. Again, such procedure may be followed a number of times during a medication therapy. Further, contamination concerns may arise when a unit dose syringe is filled from a multi-dose reservoir at the point of use. To address such concern, unit dose syringes are often filled from a multi-dose reservoir within a pharmacy department of a medical care facility utilizing a hepa-filter air hood. However, significant syringe handling is required. Moreover, labeling becomes a further need when a delay is expected between the filling of a unit dose syringe and the usage of the filled syringe.

SUMMARY OF THE INVENTION

In view of the foregoing, a primary objective of the present invention is to reduce the number of steps and associated time required by medical personnel for the infusion of medical liquids in conjunction with IV procedures. A related objective is to facilitate the utilization of multi-dose flush solution sources in conjunction with IV liquid medication administration procedures occurring over an extended course of therapy.

An additional objective of the present invention is to provide the noted medical liquid administration efficiencies in a manner that also enhances the maintenance of sterility.

A further objective of the present invention is to facilitate the utilization of different types of flush solutions, including the use of two different flush solutions in conjunction with IV procedures for a given patient.

Yet another objective of the present invention is to reduce medical waste associated with the IV administration of flush solutions.

In addressing the noted objectives, the present inventors have recognized the desirability of providing an apparatus that fluidly interconnects fluid lines from multiple medical liquid sources to a single fluid line that is selectively interconnectable to a vascular catheter access port. More particularly, the inventors have recognized that desirability of providing an apparatus that allows a liquid medication source and multiple flush solutions to be administered in a closed system through a single fluid line that entails only a single interconnection to a vascular catheter access port.

As such, one or more of the above objectives and additional advantages may be realized by an inventive medical liquid administration apparatus that comprises a valve having a control member selectively positionable to provide any selected one of a plurality of flow paths through the valve, and a syringe, fluidly interconnected to a syringe port of the valve, for receiving and dispensing medical liquid through the valve.

In one aspect, the syringe may be fixedly interconnected to the control member for clockwise and counterclockwise co-rotation therewith. In this regard, the control member may be positionable so that in a first position a first flow path between a first inlet port of the valve and the syringe port is provided. The control member may be further positionable in a second position to provide a second flow path between the syringe and an outlet port of the valve. Such selective positioning facilitates the drawing of a first medical liquid (e.g. a first flush solution) into the syringe through the first inlet port when the control member is in the first position, and the subsequent administration of such medical liquid from the syringe through the outlet port of the valve when the control member is in the second position, e.g. administration via a vascular catheter access port.

Further, the control member may be provided for selective positioning in a third position wherein a third flow path is defined between a second inlet port and the needle-less syringe. Such functionality allows for the use of the syringe to draw a second medical liquid (e.g. a second flush solution) through the second inlet port when the control member is in the third position, and the subsequent administration of the medical liquid through the outlet port of the valve when the control member is in the second position.

Of note, the valve may also include a third inlet port, wherein when the control member is in the second position a fourth flow path is defined to allow a third medical liquid (e.g. a liquid medication or drug) to be passed directly through the third inlet port to the outlet port of the valve, wherein the third medical liquid is administered to a patient, e.g. via a vascular catheter access port. In such an arrangement the second and fourth flow paths are fluidly interconnected and partially overlap.

In another aspect, a valve may be provided which includes a plurality of valve ports, including the syringe port and first and second valve inlet ports having corresponding center axes in offset first and second planes, respectively. Further, the control member may be positionable to provide any selected one of a plurality of flow paths between a corresponding plurality of different sets of the valve ports. More particularly, the control member may be provided with an internal passageway extending between a plurality of apertures in the control member, wherein a first aperture and a second aperture have corresponding center axes lying in said offset first and second planes, respectively. That is, the center axes of the first valve port and first aperture may be disposed within a common first plane, and the center axes of the second valve port and second aperture may be disposed within a common second plane. Moreover, the first and second planes may be substantially parallel. Such an arrangement allows multiple flow paths to be defined in a relatively simple manner. For example, in one embodiment at least a portion of the control member may be rotatably disposed in the valve, wherein such portion includes the first and second apertures.

In conjunction with this aspect, a first set of valve ports may be disposed in a first relative relationship and a different second set of valve ports may be disposed in a second relative relationship, said first and second relative relationships being different. Correspondingly, a first set of control member apertures may be disposed in said first relative relationship and a second set of control member apertures may be disposed in a said second relative relationship. Further, the first and second sets of apertures may each include at least one aperture in common.

As should be noted, the described administration apparatus allows up to three different medical liquid sources to be concurrently interconnected to three different inlet ports and separately administered through a common outlet port in a closed system, wherein the interconnected syringe is employable for the receipt and administration of the medical liquids. In the later regard, the outlet port may be selectively interconnected to a vascular catheter access port (e.g. via an interconnected tubing line having a male luer connector). By way of primary example, the invention allows for the sequential administration of a liquid medication, or drugs, and two different flush solutions via a closed system and pursuant to the establishment of a single vascular catheter interconnection.

Additional features may be provided in combination with the above noted apparatus. For example, the syringe port and an end aperture of the control member may be disposed in opposing, aligned relation on the center axis of the valve. Further, the control member may be provided with a plurality of side apertures that may be selectively aligned with different ones of a plurality of valve side ports. As will be appreciated, the side apertures of the control member may be disposed for selective blockage by internal sidewalls of the valve in certain positions.

Additionally, the medical liquid administration apparatus may include one or more indicators for identifying the optional fluid flow paths through the valve. For example, such indicator(s) may include visual path identifiers (e.g. corresponding with intended liquid medication and first/second solution source interconnections) located in spatial relation to inlet/outlet ports of the valve. The syringe may also be oriented transverse to a center axis of the valve, wherein the syringe may be selectively positioned in substantial alignment with a given one of the valve ports to affect a desired fluid flow path through the valve.

In yet another feature, the syringe of the administration apparatus may include a syringe body, a plunger having a bottom end disposed in a top end of the syringe body, and a sealing member for sealing the top end of the syringe body to the plunger. More particularly, the sealing member may extend from a top end of the syringe body to a top end of the plunger. By way of example, the sealing member may comprise a flexible membrane that functions in a bellows-like manner.

Various capabilities accommodated by the inventive administration apparatus may be implemented in an inventive method for medical liquid administration. In one aspect, the inventive method includes the steps of fluidly interconnecting a first flush solution source to a first inlet port of an administration apparatus, a second flush solution source to a second inlet port of the administration apparatus, and a liquid medication source to a third inlet port of the administration apparatus. The method further includes the step of passing a selected one of the flush solutions into a syringe of the administration apparatus. Of course, the inventive method may further include the step of flowing the selected flush solution from the syringe through an outlet port of the administration apparatus for administration to a patient, e.g.

via a vascular catheter access port to a patient. Additionally, the method may include the step of infusing liquid medication by passing the liquid medication from the liquid medication source into the third inlet port and out of outlet port of the administration apparatus for administration to a patient, e.g. via a vascular catheter access port to a patient. Of note, a common outlet port is utilized for both flush solution and liquid medication administration.

As may be appreciated, the inventive method may further include the steps of passing and flowing of a selected flush solution both prior to and after the liquid medication infusing step. In this regard, the first flush solution may be selected for said passing and flowing steps prior to the infusing step, and the second flush solution may be selected for the passing and flowing steps after said infusing step. More particularly, the first flush solution may include a saline solution and the second flush solution may comprise a heparin solution.

In multiple-dose applications, the inventive method may include repeating the passing, flowing and infusing steps a desired number of times, while maintaining at least one of the fluid interconnections at the first, second and third inlet ports of the medical liquid administration apparatus. Moreover, the passing, flowing and infusing steps may be repeated any number of times while maintaining all three of the medical liquid source/inlet port interconnections. The maintenance of such interconnections yields sterility benefits as well as reduced procedural requirements.

In conjunction with multiple-dose applications, the inventive method may further include the steps of interconnecting the outlet port of the administration apparatus to a vascular catheter access port to a patient, completing the flowing and infusing steps noted above, and disconnecting the outlet port of the medical liquid administration apparatus from the vascular catheter access port to the patient. In turn, the interconnecting, completing and disconnecting steps may be repeated a number of times. As will be appreciated, such steps accommodate the ambulatory needs of a patient receiving medication therapy over an extended time period, while also reducing the overall member of vascular catheter interconnections/disconnections required for liquid medication infusion and pre/post flushing procedures.

In relation to the step of passing a selected flush solution into the syringe, such step may include a selected one of establishing: (i) a first closed flow path between the first inlet port and syringe, and (ii) a second closed path between the second inlet port and the syringe. Further, the step of flowing the selected flush solution to a vascular catheter access port may provide for the establishment of a third flow path between the syringe and the outlet port. The noted methodology may be implemented so that only one of the first, second or third flow paths is establishable at a given time. Further, the noted establishment of first, second or third flow paths may be selectively established via the rotation of a control member within a valve of the administration apparatus. Further, such rotating step may include the alignment of the syringe with one of the first, second and third inlet ports to establish a corresponding selected one of the first, second and third flow paths. Visual path identifiers (as noted above) may also be obscured in conjunction with the selection of a desired flow path.

In completing the step of passing a selected flush solution into the syringe of the administration apparatus, the selected flush solution may be drawn by the retraction of a plunger relative to a barrel of the syringe. In turn, the step of flowing the selected flush solution out the outlet port, e.g. to a vascular catheter access port, may entail advancement of the plunger relative to the barrel of the syringe.

As may be appreciated, the method may further provide for the retraction of the syringe plunger relative to the syringe barrel after at least one or both of the steps of flowing the selected flush solution or infusing the liquid medication. In conjunction with such retraction, the method may also include the step of observing fluid drawn from a patient towards a vascular catheter access port, wherein a proper fluid interconnection at the vascular catheter may be confirmed.

Additional aspects and advantages of the present invention will become apparent to those skilled in the art upon consideration of the further description provided hereinbelow.

BRIEF DESCRIPTION OF THE DRAWINGS

FIGS. 3A and 3B are perspective and top views of the administration apparatus embodiment of FIG. 1A, as interconnected to a liquid medication source and a first flush solution source, with two flow paths being defined by the medical liquid administration apparatus.

FIG. 3C is a side cross-sectional view of the administration apparatus embodiment and liquid medication source shown in FIGS. 3A and 3B, as taken along line AA of FIG. 3A.

FIGS. 6A–6H are schematic illustrations showing various selected flow paths definable by the administration apparatus embodiment of FIG. 1A in accordance with one method embodiment of the present invention.

DETAILED DESCRIPTION

Figure 1A:
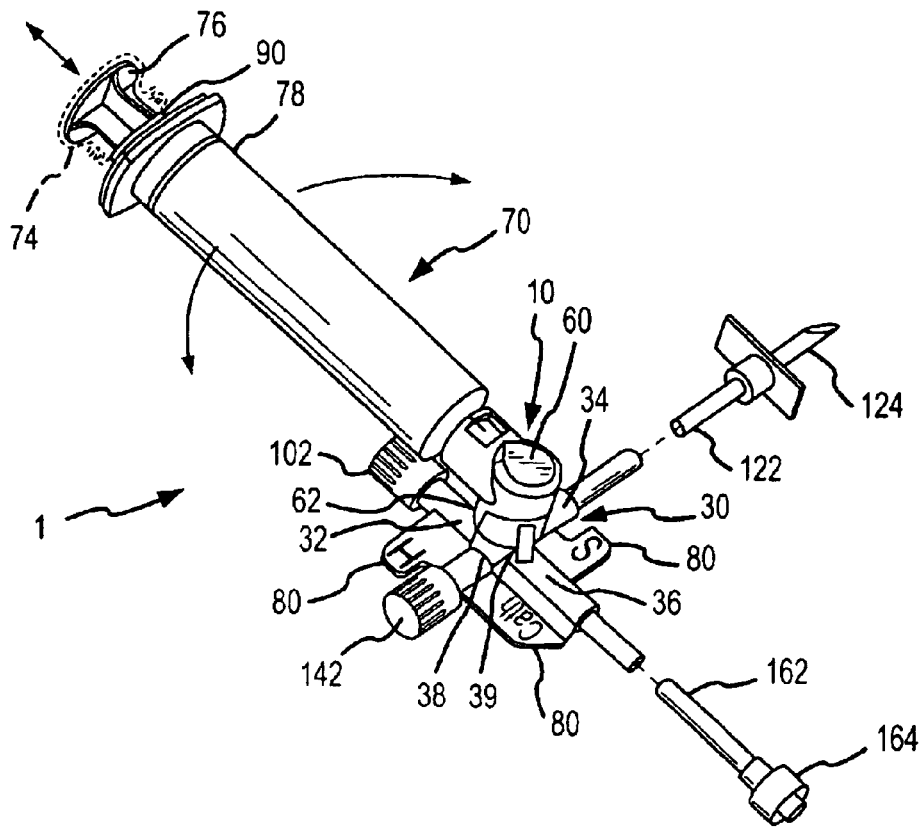
FIG. 1A is perspective view of one medical liquid administration apparatus embodiment comprising the present invention.
Figure 1B:
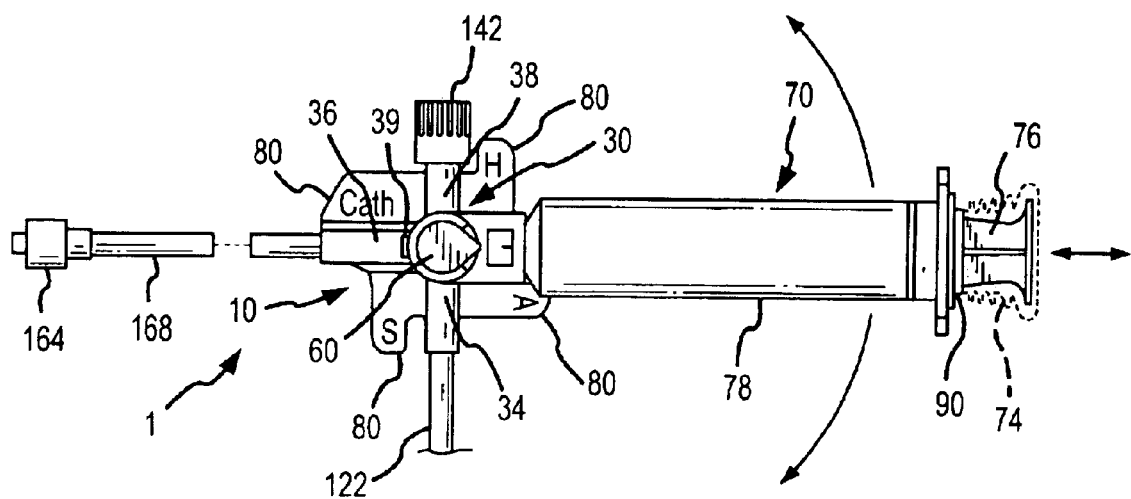
FIG. 1B is a top view of the administration apparatus embodiment of FIG. 1A.
Figure 1D:
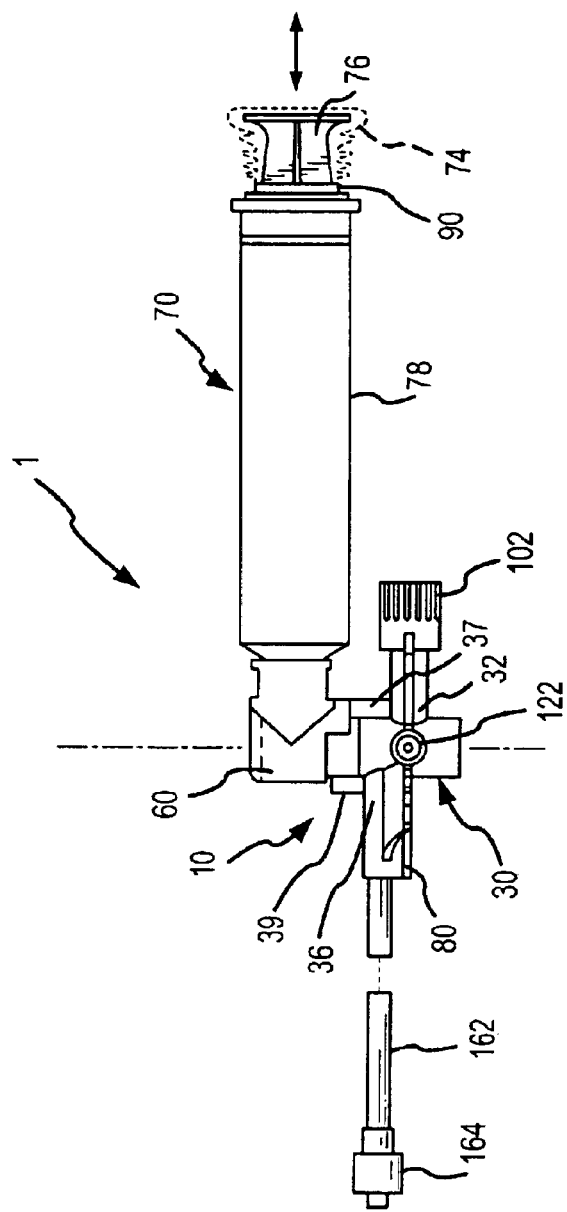
FIG. 1D is a side view of the administration apparatus embodiment of FIG. 1A.
Figure 1C:
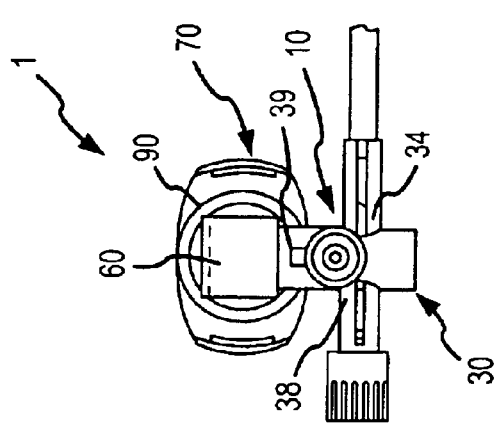
FIG. 1C is a front view of the administration apparatus embodiment of FIG. 1A.
Figure 2:
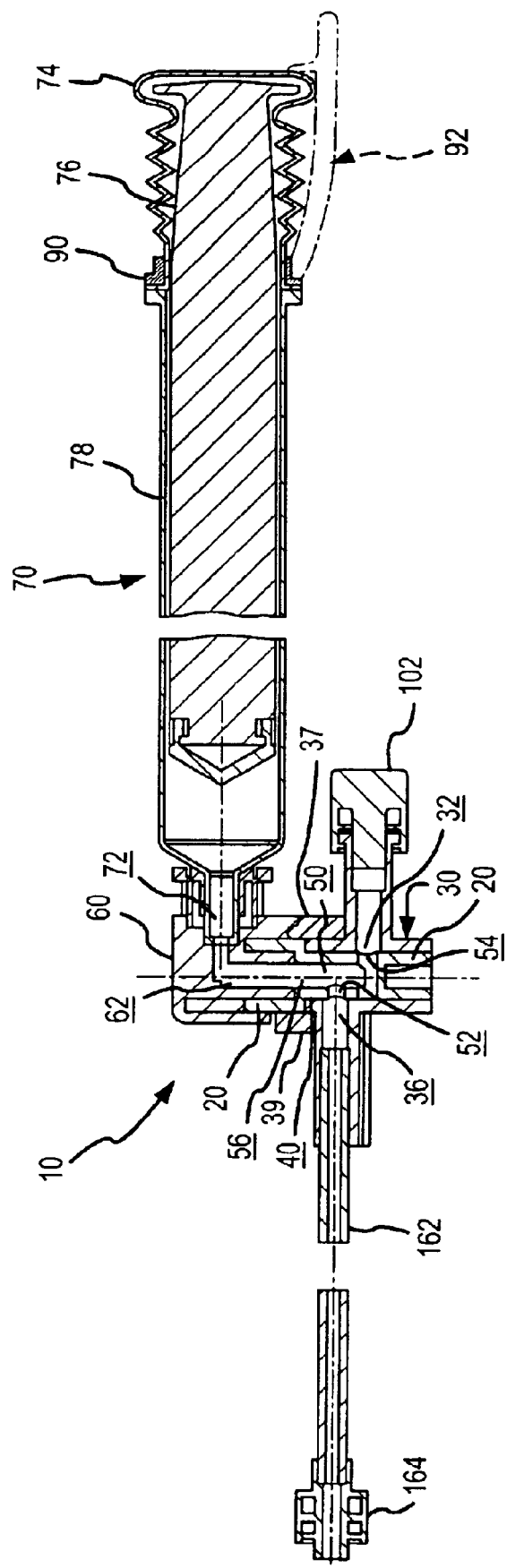
FIG. 2 is a cross-sectional side view of the administration apparatus embodiment of FIG. 1A, with a syringe thereof shown in a first position.

FIGS. 1A–1D and 2 illustrate one medical liquid administration apparatus embodiment comprising various features of the present invention. The administration apparatus 1 includes a valve 10 and a syringe 70 fluidly interconnected to the valve 10. As best shown by FIG. 2, the valve 10 includes a control member 20 rotatably disposed within a valve housing 30. The control member 20 may be selectively rotated relative to valve housing 30 to provide a number of flow paths through the valve 10.

In this regard, valve housing 30 is provided with side ports 32, 34, 36, 38, as well as a syringe port 40. Control member 20 includes an internal passageway 50 that extends between apertures 52, 54 and 56. As will be further described, apertures 54 and 56 are disposed to provide for the selective passage of medical liquids between side ports 34 and 38, and syringe port 40. Apertures 52 and 56 are disposed to provide for the selective passage of medical liquids between syringe port 40 and side port 36. Apertures 52 and 54 are further disposed to provide for the direct passage of a medical liquid between side port 32 and side port 36.

The syringe 70 may be fixedly interconnected through syringe port 40 to the control member 20, e.g. via an interconnection member 60, for clockwise and counter-clockwise co-rotation with the control member 20. In one arrangement, a cylindrical end of control member 20 may be located and adhered within a complimentary, annular groove of the interconnection member 60 to achieve interconnection. A fluid opening 62 may be defined through the interconnection member 60 to fluidly interconnect aperture 56 and a fluid port 72 of the syringe 70.

As noted, various flow paths through valve 10 may be selectively established. Such capability allows medical liquid administration apparatus 1 to be utilized for the administration of three (3) different medical liquids, e.g. via an interconnectable vascular catheter access port. Furthermore, integration of syringe 70 in medical liquid administration apparatus 1 facilities the administration of a medical liquid from one or a plurality of interconnected sources (e.g. containing different flush solutions) on a successive, repeated basis during the course of medication therapy for a given patient. In particular, medical liquid administration apparatus 1 may be employed for the successive administration of a catheter flush solution, such as a saline solution and/or heparin solution, before and/or after liquid medication infusions, wherein at least one of the flush solutions is contained in an interconnectable reservoir of sufficient volume to dispense multiple flush solution dosages.

Referring now to FIGS. 1A–1D and 2, the spatial relationships between valve ports 32, 34, 36, 38, 40 and apertures 52, 54 and 56 of control member 20 will be described. In particular, valve side ports 32, 34, 38 have corresponding center axes disposed in a common first plane, and valve side port 36 has a center axis disposed in a second plane offset from and parallel to the first plane. Correspondingly, control member 20 is disposed within valve housing 30 so that the center axes of apertures 52, 54 are disposed in said offset first plane and second plane, respectively. Further, valve port 40 and aperture 56 are disposed in opposing aligned relation on a center axis of valve housing 30.

In connection with the foregoing, and as best shown in FIG. 1B and FIG. 2 it should also be noted that the center axes of the valve side ports 32, 34, 36, 38 and the center axes of apertures 52, 54 of control member 20 are disposed to facilitate various aligned relationships therebetween. In particular, the center axes of coplanar ports 32, 34 and 38 are offset at 90° intervals about the center axis of valve housing 30. On the other hand, apertures 52 and 54 of control member 20 are offset 180° about the center axis of valve housing 30.

By virtue of noted relative relationships, control member 20 may be rotatably positioned relative to valve housing 30 to selectively provide for the passage of liquid between port 34 and port 40 in a first position, between port 38 and port 40 in a second position, and between port 40 and port 36 in a third position. Additionally, when in the third position control member 20 also provides for direct passage of liquid between port 32 and port 36. Further in this regard, it should be noted that when the control member 20 is positioned in each of the first and second positions, aperture 52 is blocked by an internal sidewall of valve housing 30, thereby preventing the passage of liquid therethrough.

In addition to the above-noted features, administration apparatus 1 may further include flow path indication, sterility maintenance and fluid interconnection features. In particular, administration apparatus 1 may include visual representations disposed in spatial relation to valve side ports 32, 34, 36 and 38 that correspond with the intended fluid interconnections. For example, as shown in FIGS. 1A and 1B the letters "S", "A" and "H" may be disposed in spatial relation to ports 34, 32 and 38, respectively, wherein the "S" port 34 is intended for fluid interconnection with a saline flush solution source, the "A" port 32 is intended for fluid interconnection with a liquid medication source, and the "H" port 38 is intended for fluid interconnection with a heparin flush solution source. As further shown by FIGS. 1A and 1B, the visual representation "Cath" is provided in spatial relation to valve side port 36, wherein the "Cath" port 36 is intended for fluid interconnection with a patient, e.g. a vascular catheter access port to a patient. In medical liquid administration apparatus 1, the various visual representations noted above are provided on web members 80. Certainly, other embodiments may utilize alternate visual representations disposed in other locations, e.g. directly on port extension members.

In conjunction with the foregoing, it should also be noted that syringe 70 is disposed transverse to the center axis of the valve 10 (e.g. substantially parallel to the center axes of the various valve side ports 32, 34, 36, 38), wherein syringe 70 is rotatable about the center axis of the valve 10 to obtain the desired flow path through valve 10. That is, by rotating syringe 70 over and into an aligned relation with a given one of the valve side ports 32, 34 and 38, the fluid flow path corresponding with such valve side port may be achieved. In this regard, valve 10 may be provided so as to mechanically restrict the rotatable positioning of control member 20 to an arc that extends between ports 32, 34 and 38 (e.g. at least 180°) but which does not extend by port 36. For example, and as best shown by FIG. 1D, valve housing 30 may include an upstanding stop member 39 that extends into a cut-Out region of a bottom skirt of interconnection member 60. In turn, rotation of the interconnection member 60 and control member 20 is limited to the arc defined by the cut-out region of interconnection member 60. To facilitate aligned positioning of control member 20, valve housing 30 may also include an upstanding detent member 37 having a rounded top end for receipt by a complimentary depression (e.g. hemispherical) in the bottom skirt of the interconnection member 60. As will be appreciated, when control member is rotatably positioned into the above-noted third position (e.g. to define passageways between ports 40 and 36 and between ports 32 and 36), the rounded top end of detent member 37 will slidably pass into the complimentary depression of bottom skirt.

To facilitate repeated use of the syringe 70 during a given medication therapy, syringe 70 is provided with a sealing member 74 for maintaining sterility. More particularly, the sealing member 74 may extend over the top end of the plunger 76 and interconnected with the syringe body 78, e.g. via a securing ring 90 interconnected to a top end of the syringe body 78. Sealing member 74 may be a collapsible membrane that functions in a bellows-like manner to facilitate advancement and retraction of plunger 76 relative to syringe body 78. As will be appreciated, the provision of sealing member 74 maintains the sterility of the inside surfaces of the syringe body 78 during use.

More generally in this regard, it may be appreciated that the medical liquid administration apparatus 1 may be packaged in a sterile condition. For example, the administration apparatus 1 may be assembled, packaged in a heat-sealed enclosure, and sterilized via exposure to gamma radiation.

As shown in phantom in FIG. 2, a catch member 92 may also be provided with administration apparatus 1. For example, catch member 92 may be interconnected to or comprise a further feature of securing ring 90. In use, the catch member 92 may be employed to selectively restrict retraction of plunger 76 relative to syringe body 78. Such feature may be of particular use during use of the administration apparatus 1 for liquid medication administration. Of course, catch member 92 may also be deflected outward to permit use of the plunger 76, as will be described.

As indicated, the medical liquid administration apparatus 1 may be further provided with a number of features to facilitate various intended fluid interconnections. In particular, and as best shown by FIGS. 1A–1D, 3A, 4A and 5A, administration apparatus 1 may be provided with a tubing line 122 connected to valve side port 34. In turn, tubing line 122 may be directly connected to a first flush solution source 120 (e.g. a saline solution reservoir) or may be provided with a spike member 124 for selective interconnection to a vial or other reservoir containing a first flush solution (e.g. saline flush solution). Administration apparatus 1 may also be provided with a lure connector 102 (e.g. a female luer connector having a removable cap) connected to valve side port 32 for selective interconnection with a complimentary lure connector 104 (e.g. a male luer connector) that is provided at one end of a tubing line 106 fluidly interconnected to a liquid medication source 100. A clip 108 may be provided on tubing line 106 for selective occlusion of tubing line 106. Administration apparatus 1 may also be provided with a lure connector 142 (e.g. a female luer connector having a removable cap) connected to valve side port 38 for selective interconnection with a complementary lure connector 146 (e.g. a male luer connector) provided at one end of a tubing line 144 interconnected with a second flush solution source 140 (i.e. a heparin flush solution). Finally, administration apparatus 1 may also be provided with a tubing line 162 connected to valve side port 36 and having a male lure connector 164, e.g. provided for selective interconnection with a complementary female luer connector comprising a vascular catheter access port 160 to a patient.

Such various fluid interconnection features will now be further described in relation to intended exemplary applications. With specific reference to FIGS. 3A, 3B and 3C, the administration apparatus 1 is shown with syringe 70 located in a position to define a flow path between the liquid medication source 100 and vascular catheter access port 160 via valve ports 32 and 36. To administer liquid medication, the liquid medication source 100 may be controlled to infuse the medical liquid into the vascular catheter access port 160. For example, when liquid medication source 100 comprises a syringe, the plunger may be advanced relative to the barrel thereof to achieve administration. In one approach, the liquid medication source 100 may be mounted in an automated device 110 for automated dispensation of pre-selected dosage amounts. As noted above, during liquid medication administration the optional catch member 92 may be positioned to restrict retraction of the syringe plunger 76. Preferably, clip 108 is manipulated to occlude, or close, tubing line 106 during all periods between liquid medication administrations.

Figure 3A:
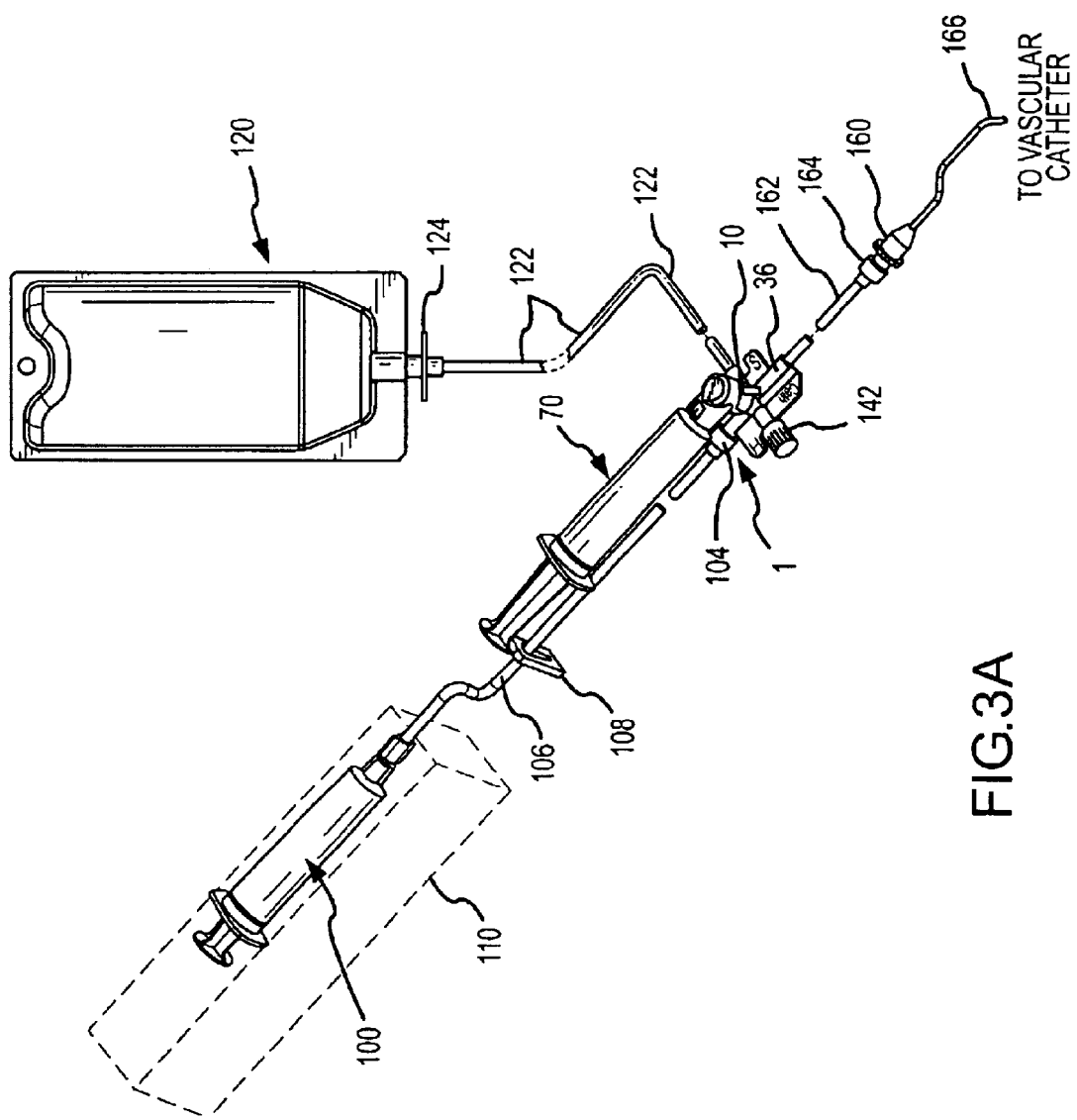

When syringe 70 is located in the position shown in FIGS. 3A, 3B and 3C, a flow path is also defined between syringe 70 and vascular catheter access port 160 via valve ports 40 and 36. As will be described, such position is employed to administer first or second flush solution amounts drawn into syringe 70.

Figure 4A:
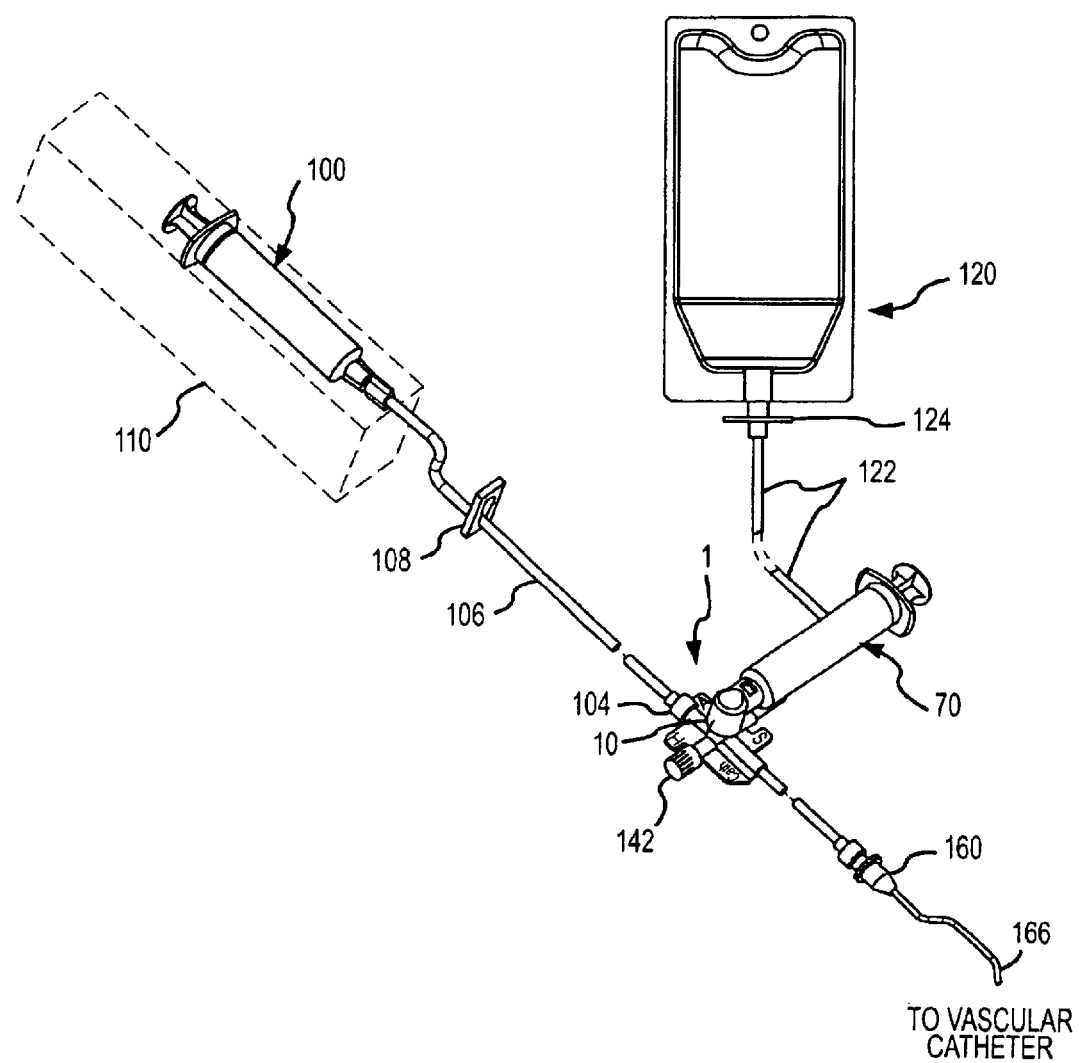
FIGS. 4A and 4B are perspective and top views of the administration apparatus embodiment of FIG. 1A, as interconnected to a liquid medication source and a first flush solution source, with another flow path being defined by the administration apparatus.
Figure 4B:
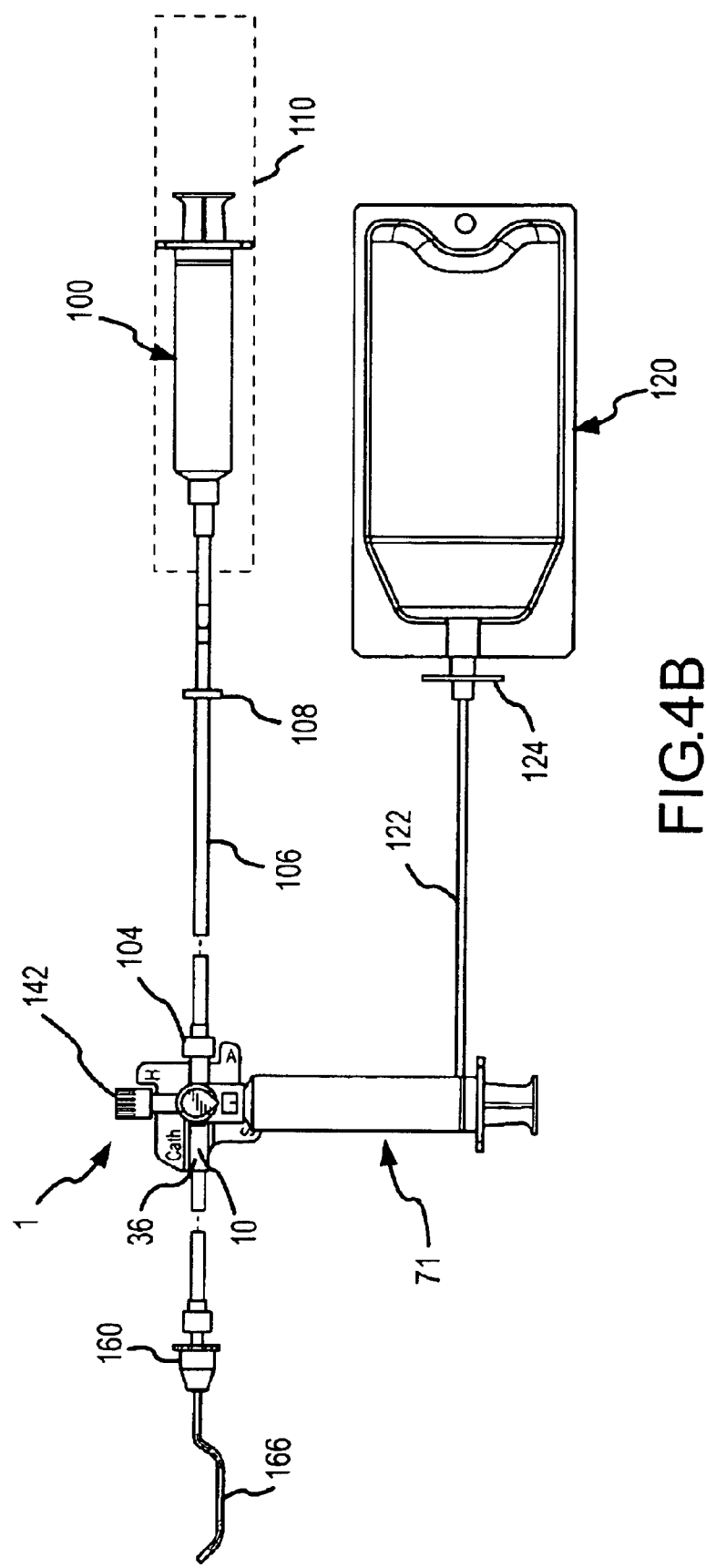

In that regard, and referring now to FIGS. 4A and 4B, syringe 70 is shown in a position that provides a fluid flow path between the first flush solution source 120 and syringe 70 via valve ports 34 and 40. To facilitate the passage of the first flush solution into the syringe 70, plunger 76 is retracted so as to draw the flush solution through the tubing line 122 and valve 10 into the syringe body 78. To administer the first flush solution from the syringe body 78, syringe 70 is rotated into the position shown in FIG. 3A–3C. Thereafter, plunger 76 may be advanced so as to flow the flush solution through valve ports 40, 36 to the vascular catheter access port 160.

Figure 5A:
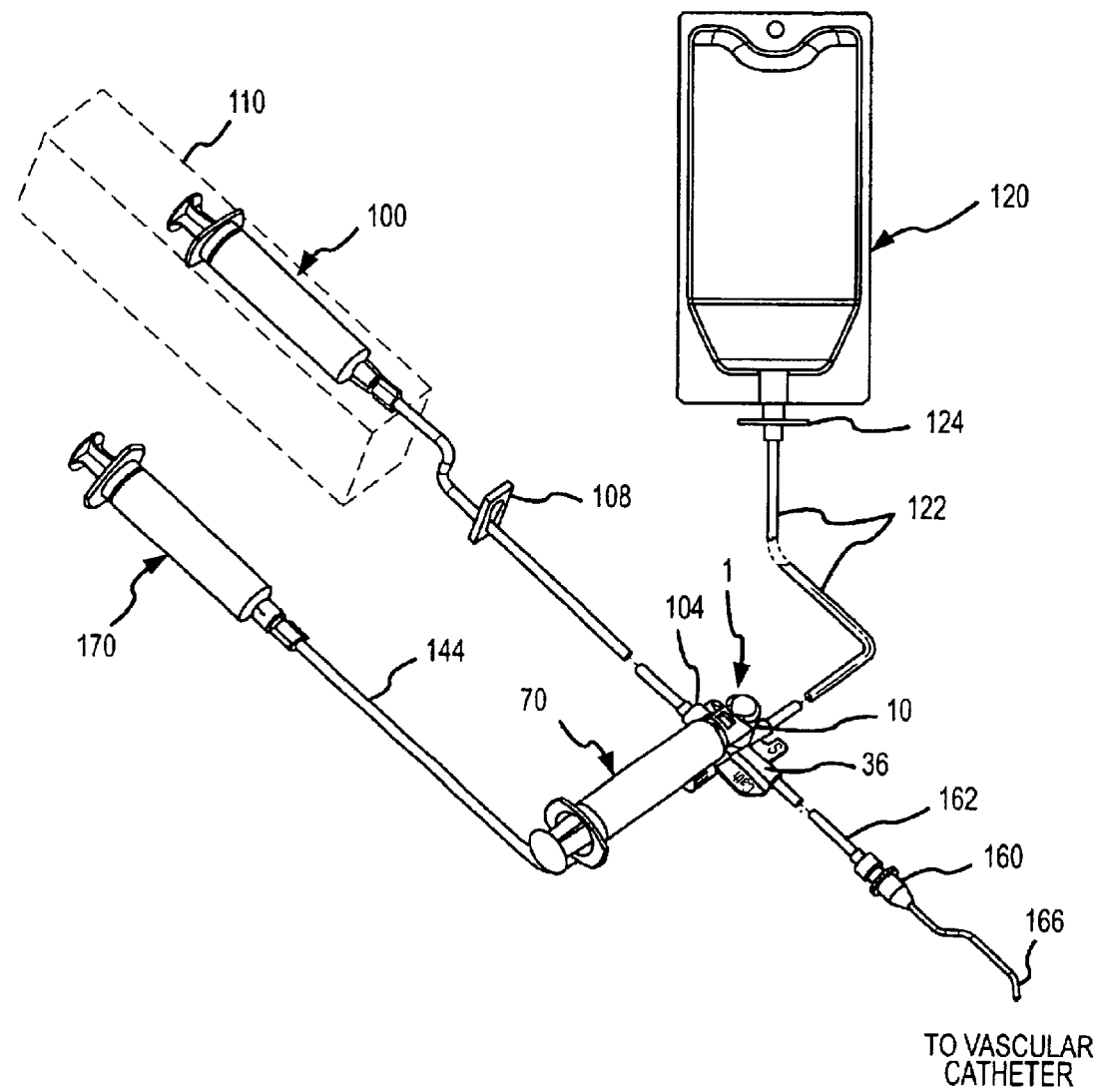
FIGS. 5A and 5B are perspective and top views of the administration apparatus embodiment of FIG. 1A, as interconnected to a liquid medication source and first and second flush solution sources, with yet another flow path being defined by the administration apparatus.
Figure 5B:
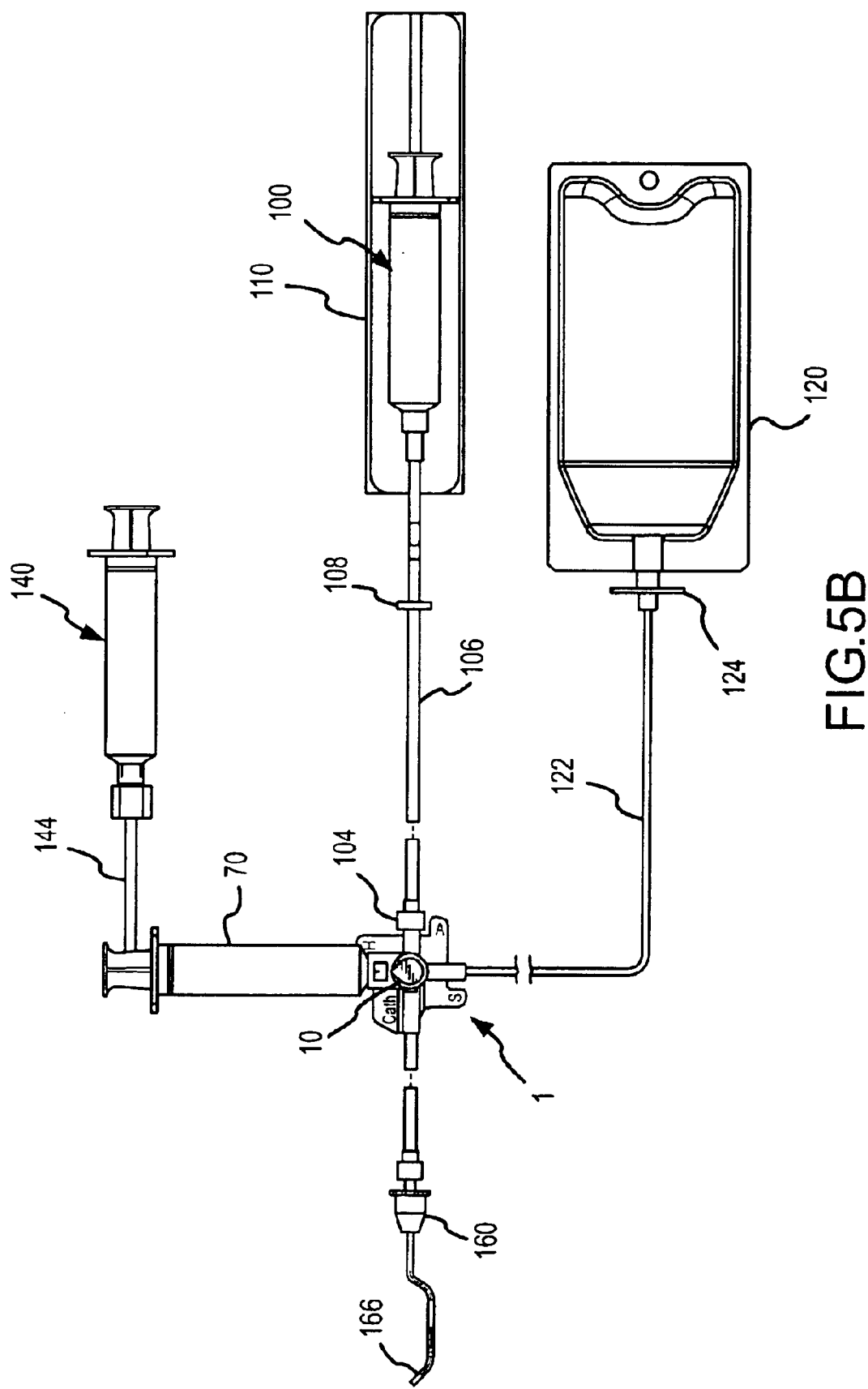

A similar procedure may be followed for optional usage of the second flush solution source 140. More particularly, and referring now to FIGS. 5A and 5B, syringe 70 is shown in a position that provides a fluid path between the second flush solution source 140 and syringe 70 via valve ports 38 and 40. In this position plunger 76 of syringe 70 may be retracted to draw flush solution from source 140. Then, syringe 70 may be rotated to the position shown in FIGS. 3A–3C for infusion of the second flush solution through vascular catheter access port 160.

Of note, it should be appreciated that, prior to or after the infusion of a liquid medication or flush solution, administration apparatus may be conveniently employed for effective vascular catheter aspiration. In particular, syringe plunger 76 may be retracted to manually draw a small amount of blood through an interconnected vascular catheter and into tubing line 166 to allow medical personnel to confirm proper catheter placement and/or the absence of blood clotting. Then, syringe plunger 76 may be advanced to return the blood.

An exemplary procedure using the medical liquid administration apparatus 1 will now be presented. To begin the procedure the liquid administration apparatus 1 is removed from sterile packaging and set-up procedures completed. In particular, and with reference to FIGS. 3A, 4A and 5A, a vascular catheter access port 160 may be fluidly interconnected to the medical liquid administration apparatus 1 via male luer connector 164, tubing line 162 and valve side port 36. Further, liquid medication source 100 may be fluidly interconnected to side port 32 of the medical liquid administration apparatus 1, and source 100 may be optionally positioned within an automated infusion device 110 as deemed appropriate by medical personnel. To complete the set-up procedure, a saline flush solution source 120 and/or heparin flush solution source 140 may be fluidly interconnected to valve side port 34 and/or valve side port 38 of the medical liquid administration apparatus 1. At this point, all necessary fluid interconnections have been made to allow for the use of medical liquid administration apparatus 1 on a repeated basis over the course of an extended medication therapy.

Following setup, various tubing lines comprising the various fluid interconnections may be primed by sequentially positioning and control of syringe 70 to define and draw liquid through the desired fluid flow path to be primed both upstream of the medical liquid administration apparatus 1 and downstream thereof. Tubing line 106 may be primed by manipulation or automated control of liquid medication source 100. Next, a vascular catheter (not shown) interconnected via tubing line 166 to vascular catheter access port 160 may be inserted into a patient. Then, syringe 70 may be employed to aspirate the vascular catheter.

Reference is now made to FIG. 1A and FIGS. 6A–6H. When medical personnel determine that it is an appropriate time to provide a dose of liquid medication, the syringe 70 may be aligned with port 34 to define a fluid flow path between the saline flush solution source 120 and the syringe 70 via valve 10, see FIG. 6A. Medical personnel may then pass a desired volume of the saline flush solution into the syringe 70 via retraction of plunger 76. Next, medical personnel may locate the syringe 70 into an aligned orientation with port 36, see FIG. 6B. The plunger 76 may then be advanced to flow the saline flush solution through the valve 10 and into the vascular catheter access port 160 to the patient. Of note, plunger 76 may then be retracted a sufficient amount to allow medical personnel to visually confirm a blood return into the vascular catheter access port tubing line 166, see FIG. 6C. Upon such confirmation, plunger 76 may be advanced to push the blood back into the patient.

Next, medical personnel may position the syringe 70 in an aligned orientation with valve side port 32, see FIG. 6D. Concomitantly, clip 108 may be positioned to open the tubing line 106 and a predetermined, desired amount of liquid medication may be passed from liquid medication source 100 into vascular catheter access port 160 via manipulation or automated control of liquid medication source 100. Clip 108 may then be repositioned to occlude tubing line 106. Again, plunger 76 may be retracted a sufficient amount to allow medical personnel to visually confirm a blood return into the vascular catheter access port tubing line 166. Upon such confirmation, plunger 76 may be advanced to push the blood back into the patient.

When the desired liquid medication infusion is complete, medical personnel may rotate the syringe 70 into an aligned position with port 34, see FIG. 6E. A desired volume saline flush solution may be drawn from source 120 into the syringe 70. Syringe 70 may then be rotated back into an aligned position with port 36, see FIG. 6F, and plunger 76 advanced to affect passage of the saline flush solution through the administration apparatus 1 to vascular catheter access port 160. Medical personnel may then slightly retract plunger 76 to again visually confirm a blood return within the vascular access port tubing 166, as per FIG. 6C, and thereafter push the blood back into the patient.

As may be appreciated, when use of the heparin flush solution from source 140 is desired, the syringe 70 may be oriented in an aligned relation with a port 38, see FIG. 6G. hereafter, the heparin flush solution may be passed into the syringe 70 and subsequently infused by rotating the syringe 70 into an aligned orientation with port 36, see FIG. 6H, and advancing plunger 76.

After a given infusion of liquid medication is completed, the valve side port 36 of medical liquid administration apparatus 1 may be selectively disconnected from the vascular catheter access port 160, e.g. male luer connector 164 may be disconnected and covered. For example, the male luer connector 164 may be temporarily docked within a docking apparatus such as that described in U.S. patent application Ser. No. 10/226,183, entitled "STERILE DOCKING APPARATUS AND METHOD", filed Aug. 22, 2002, hereby incorporated by reference in its entirety.

When a further infusion of liquid medication is desired, the male lure connector 164 may be uncovered. The male luer connector 164 and vascular catheter access port 160 may then be swabbed with an appropriate anti-bacterial solution and reconnected. Thereafter, the procedure may continue as per the description accompanying FIGS. 6A–6H above.

In accordance with described arrangement, multiple infusions of liquid medication may be completed utilizing medical liquid administration apparatus 1, while maintaining fluid interconnections between the medical liquid administration apparatus 1 and saline flush solution source 120, liquid medication source 100 and/or heparin flush solution source 140. As may be appreciated, the maintenance of one or more such interconnections simplifies the overall procedure for medical personnel, results in reduced waste relative to prior techniques, and enhances the maintenance of sterile interconnections.

The embodiments described above are for exemplary purposes only and is not intended to limit the scope of the present invention. Various adaptations, modifications and extensions of the described system/method will be apparent to those skilled in the art and are intended to be within the scope of the invention as defined by the claims which follow.

What is claimed is:

1. An apparatus for medical liquid administration comprising:

a valve having a control member selectively positionable to provide any selected one of a plurality of flow paths through said valve; and, a syringe, fluidly interconnected to a syringe port of said valve for receiving and administering liquid through said valve, and fixedly interconnected to said control member for clockwise and counterclockwise co-rotation therewith.

2. An apparatus as recited in claim 1, wherein:

in a first selectable position said control member provides a first flow path between a first inlet port of said valve and said syringe port; and, in a second selectable position said control member provides a second flaw path between said syringe port and an outlet port of said valve.

3. An apparatus as recited in claim 1, wherein:

in a third selectable position said control member provides a third flow path between a second inlet port and said syringe port.

4. An apparatus as recited in claim 3, wherein:

in said second selectable position said control member provides a fourth flow path between a third inlet port and said outlet port.

5. An apparatus as recited in claim 4, further comprising:

a connector adapted for selective interconnection of said first inlet port to a first flush solution source;

a second connector adapted for selective interconnection of said outlet port to a vascular catheter access port; and, a third connector adapted for selective interconnection of said third inlet port to a liquid medication source.

6. An apparatus as recited in claim 5, further comprising:

a fourth connector adapted for selective interconnection of said second inlet port to a second flush solution source.

7. An apparatus as recited in claim 1, said valve further including:

a valve housing having a plurality of valve ports, wherein a first valve port and a second valve port of said plurality have corresponding center axes lying in first and second planes, respectively.

8. An apparatus as recited in claim 7, said control member including:
  an internal passageway extending between a plurality of apertures, wherein a first aperture and a second aperture of said plurality of apertures have corresponding center axes lying in said first and second planes, respectively.

9. An apparatus as recited in claim 1, further comprising:
  an indicator for indicating any selected one of said plurality of flow paths through said valve.

10. An apparatus as recited in claim 9, wherein said indicator is interconnected to said control member for co-rotation therewith.

11. An apparatus as recited in claim 1, said syringe including:
  a syringe body;
  a plunger having a bottom end slidably disposed in a top end of the syringe body; and,
  a sealing member for sealing said top end of the syringe body.

12. An apparatus as recited in claim 1, said sealing member including:
  a flexible membrane interconnected about and between said top end of the syringe body and said plunger.

13. An apparatus as recited in claim 1, said valve further including:
  a valve housing having a plurality of valve ports, wherein at least a portion of said control member is rotatably disposed within said valve housing to provide any selected one of said plurality of flow paths between a corresponding plurality of different sets of said plurality of valve ports.

14. An apparatus as recited in claim 13, said control member including:
  an internal passageway extending between a plurality of apertures.

15. An apparatus as recited in claim 14, wherein two valve ports comprising a first set of said plurality of different sets are disposed in a first relative relationship and two valve ports comprising a second set of said different sets are disposed in a second relative relationship, and wherein a first set of said plurality of apertures are disposed in said first relative relationship and a second set of said plurality of apertures are disposed in said second relative relationship.

16. An apparatus as recited in claim 15, wherein said first and second sets of said plurality of apertures each include at least one aperture in common.

17. An apparatus as recited in claim 15, wherein two valve ports comprising a third set of said different sets are disposed in one of said first and second relationships.

18. An apparatus as recited in claim 15, wherein two valve ports comprising a fourth set of said different sets are disposed in one of said first and second relationships.

19. An apparatus as recited in claim 14, wherein said portion of said control member is retainably disposed at a set location along and rotatable about the center axis of said valve housing.

20. An apparatus as recited in claim 19, wherein said syringe port and a first aperture of said plurality of apertures are disposed in opposing, aligned relation on said center axis of the valve housing.

21. An apparatus as recited in claim 20, wherein a second aperture and a third aperture of said plurality of apertures are offset from said center axis of said valve housing and have corresponding center axes lying in offset, parallel planes.

22. An apparatus as recited in claim 13, wherein said control member is selectively positionable to provide at least two different flow paths between said syringe port and corresponding different ones of said plurality of valve ports.

23. An apparatus as recited in claim 22, wherein said control member is selectively positionable to provide at least four different flow paths between different ones of said plurality of valve ports.

24. An apparatus as recited in claim 22, wherein first, second and third valve ports are disposed at arcuately offset locations about a center axis of the valve housing.

25. An apparatus as recited in claim 24, said control member including:
  an internal passageway extending between a plurality of apertures, wherein only one of said plurality of apertures and one of said first and second valve ports are alignable at a time.

26. An apparatus as recited in claim 25, wherein said syringe port and an aperture of said plurality of apertures are maintained in opposing, aligned relation at all times.

27. An apparatus as recited in claim 13, wherein said control member is selectively positionable to provide at least three different flow paths between said syringe port and corresponding different ones of said plurality of valve ports.

28. An apparatus for medical liquid administration comprising:
  a valve housing having a plurality of valve ports, wherein a first valve port and a second valve port of said plurality of valve ports have corresponding center axes lying in offset first and second planes, respectively;
  a syringe, fluidly interconnected to a syringe port of said plurality of valve ports, for receiving and dispensing liquid through said syringe port; and,
  a control member having at least a portion selectably positionable within said valve housing to provide any selected one of a plurality of flow paths between a corresponding plurality of different sets of said plurality of valve ports, said control member including an internal passageway extending between a plurality of apertures, wherein a first aperture and a second aperture of said plurality of apertures have corresponding center axes lying in said offset first and second planes, respectively, and wherein said plurality of apertures comprises at least three apertures.

29. An apparatus for medical liquid administration as recited in claim 28, wherein said potion of said control member is retainably disposed at set location along and rotatable about the center axis of said valve housing.

30. An appparatus for medical liquid administration as recited in claim 28, wherein two valve ports comprising a first set of said plurality of different sets are disposed in a first relative relationship and two valve ports comprising a second set of said different sets are disposed in a second relative relationship, and wherein a first set of said plurality of apertures are disposed in said first relative relationship and a second set of said plurality of apertures are disposed in said second relative relationship.

31. An apparatus for medical liquid administration as recited in claim 30, wherein said first and second sets of said plurality of apertures each include at least one aperture in common.

32. An apparatus for medical liquid administration as recited in claim 30, wherein two valve ports comprising a third set of said different sets are disposed in one of said first and second relative relationships.

33. An apparatus for medical liquid administration as recited in claim 30, wherein the valve ports comprising a fourth set of said different sets are disposed in one of said first and second relative relationships.

34. An apparatus for medical liquid administration as recited in claim 28, wherein said portion of said control member is retainably disposed at a set location along and rotatable about the center axis of said valve housing.

35. An apparatus for medical liquid administration as recited in claim 34, wherein said syringe port and a third aperture of said plurality of apertures are disposed in opposing relation on said center axis of the valve housing.

36. An apparatus for medical liquid administration as recited in claim 35, wherein said first aperture and said second aperture are disposed at arcuately offset locations about said center axis of said valve housing.

37. An apparatus for medical liquid administration as recited in claim 28, wherein said control member is selectively positionable to provide at least two different flow paths between said syringe port and corresponding different ones of said plurality of valve ports.

38. An apparatus for medical liquid administration as recited in claim 28, wherein said control member is selectively positionable to provide at least three different flow paths between said syringe port and corresponding different ones of said plurality of valve ports.

39. An apparatus for medical liquid administration as recited in claim 28, further comprising:

an indicator for indicating any selected one of said plurality of flow paths through said valve.

40. An apparatus for medical liquid administration as recited in claim 39, wherein said indicator is interconnected to said control member for co-rotation therewith.

41. An apparatus for medical liquid administration as recited in claim 40, wherein said syringe is fixably interconnected to said control member.

42. An apparatus for medical liquid administration as recited in claim 41, said syringe including:

a syringe body;

a plunger having a bottom end slidably disposed in a top end of the syringe body; and, a sealing member for sealing said top end of the syringe body.

* * * * *

UNITED STATES PATENT AND TRADEMARK OFFICE
CERTIFICATE OF CORRECTION

PATENT NO.    : 6,953,450 B2
DATED         : October 11, 2005
INVENTOR(S)   : Baldwin et al.

It is certified that error appears in the above-identified patent and that said Letters Patent is hereby corrected as shown below:

Column 12,
Line 38, delete "flaw" and insert -- flow --.

Column 14,
Line 47, delete "appparatus" and insert -- apparatus --.

Signed and Sealed this

Twentieth Day of December, 2005

JON W. DUDAS
*Director of the United States Patent and Trademark Office*